United States Patent
Burger et al.

(10) Patent No.: US 10,857,042 B2
(45) Date of Patent: Dec. 8, 2020

(54) NONWOVEN LAMINATE

(71) Applicant: Sandler AG, Schwarzenbach (DE)

(72) Inventors: Andreas Burger, Selb (DE); Uwe Bernhuber, Hof (DE); Wolfgang Höflich, Hof (DE)

(73) Assignee: SANDLER AG, Schwarzenbach (DE)

(*) Notice: Subject to any disclaimer, the term of this patent is extended or adjusted under 35 U.S.C. 154(b) by 207 days.

(21) Appl. No.: 15/849,833

(22) Filed: Dec. 21, 2017

(65) Prior Publication Data

US 2018/0177646 A1 Jun. 28, 2018

(30) Foreign Application Priority Data

Dec. 23, 2016 (DE) .......................... 10 2016 015 445

(51) Int. Cl.
| | | |
|---|---|---|
| A61F 13/511 | (2006.01) | |
| A61L 15/24 | (2006.01) | |
| A61L 15/26 | (2006.01) | |
| A61L 15/28 | (2006.01) | |
| A61F 13/512 | (2006.01) | |
| D04H 1/498 | (2012.01) | |
| D04H 1/495 | (2012.01) | |
| B32B 5/02 | (2006.01) | |
| B32B 5/26 | (2006.01) | |
| D04H 13/00 | (2006.01) | |
| A61F 13/51 | (2006.01) | |

(52) U.S. Cl.
CPC .... *A61F 13/51108* (2013.01); *A61F 13/5116* (2013.01); *A61F 13/5123* (2013.01); *A61F 13/5126* (2013.01); *A61F 13/51104* (2013.01); *A61L 15/24* (2013.01); *A61L 15/26* (2013.01); *A61L 15/28* (2013.01); *B32B 5/022* (2013.01); *B32B 5/26* (2013.01); *D04H 1/495* (2013.01); *D04H 1/498* (2013.01); *D04H 13/00* (2013.01); *A61F 2013/51014* (2013.01); *A61F 2013/51019* (2013.01); *A61F 2013/51026* (2013.01)

(58) Field of Classification Search
CPC .......... A61F 13/51108; A61F 13/51104; A61F 13/5126; A61F 13/5123; A61F 13/5116; A61F 2013/51014; D04H 1/46; B32B 5/26
USPC .................. 428/131–137; 442/383, 384, 402
See application file for complete search history.

(56) References Cited

U.S. PATENT DOCUMENTS

| | | | | |
|---|---|---|---|---|
| 5,658,639 A | * | 8/1997 | Curro ................ | A61F 13/00991 428/131 |
| 6,888,046 B2 | * | 5/2005 | Toyoshima .............. | D04H 1/06 604/378 |
| 7,005,558 B1 | * | 2/2006 | Johansson ............. | A61F 13/512 604/370 |

(Continued)

FOREIGN PATENT DOCUMENTS

| | | |
|---|---|---|
| DE | 1013627 B | 8/1957 |
| DE | 102006033071 A1 | 1/2008 |

(Continued)

*Primary Examiner* — Jennifer A Gillett
(74) *Attorney, Agent, or Firm* — Fox Rothschild LLP

(57) ABSTRACT

Disclosed is a nonwoven laminate having a texture for improved absorption and distribution of body liquids in sanitary products. The absorption and distribution effect is caused by perforations distributed in a pattern-like manner in combination with elevations present on one side of the nonwoven laminate.

19 Claims, 3 Drawing Sheets

(56) References Cited

U.S. PATENT DOCUMENTS

| | | | | |
|---|---|---|---|---|
| 2002/0068150 A1* | 6/2002 | Taneichi | ............... | A61F 13/494 |
| | | | | 428/138 |
| 2005/0228353 A1* | 10/2005 | Thomas | ............ | A61F 13/15731 |
| | | | | 604/385.01 |
| 2008/0045915 A1* | 2/2008 | Noda | ....................... | D04H 1/42 |
| | | | | 604/367 |
| 2014/0039437 A1* | 2/2014 | Van De Maele | ... | A61F 13/5323 |
| | | | | 604/384 |
| 2014/0121621 A1 | 5/2014 | Kirby et al. | | |
| 2014/0121624 A1* | 5/2014 | Kirby | ............... | A61F 13/51108 |
| | | | | 604/383 |
| 2015/0122269 A1* | 5/2015 | Cree | ..................... | A41D 13/11 |
| | | | | 128/863 |

FOREIGN PATENT DOCUMENTS

| | | |
|---|---|---|
| DE | 102008029057 A1 | 12/2009 |
| DE | 10296874 B4 | 2/2014 |
| DE | 102013111499 A1 | 4/2015 |
| EP | 423619 A1 | 4/1991 |
| EP | 2034072 A1 | 3/2009 |
| WO | WO-2009152791 A1 * 12/2009 ............... D04H 3/11 |
| WO | 2014068492 A1 | 5/2014 |
| WO | 2016/040618 A2 | 3/2016 |
| WO | 2017/156200 A1 | 9/2017 |

* cited by examiner

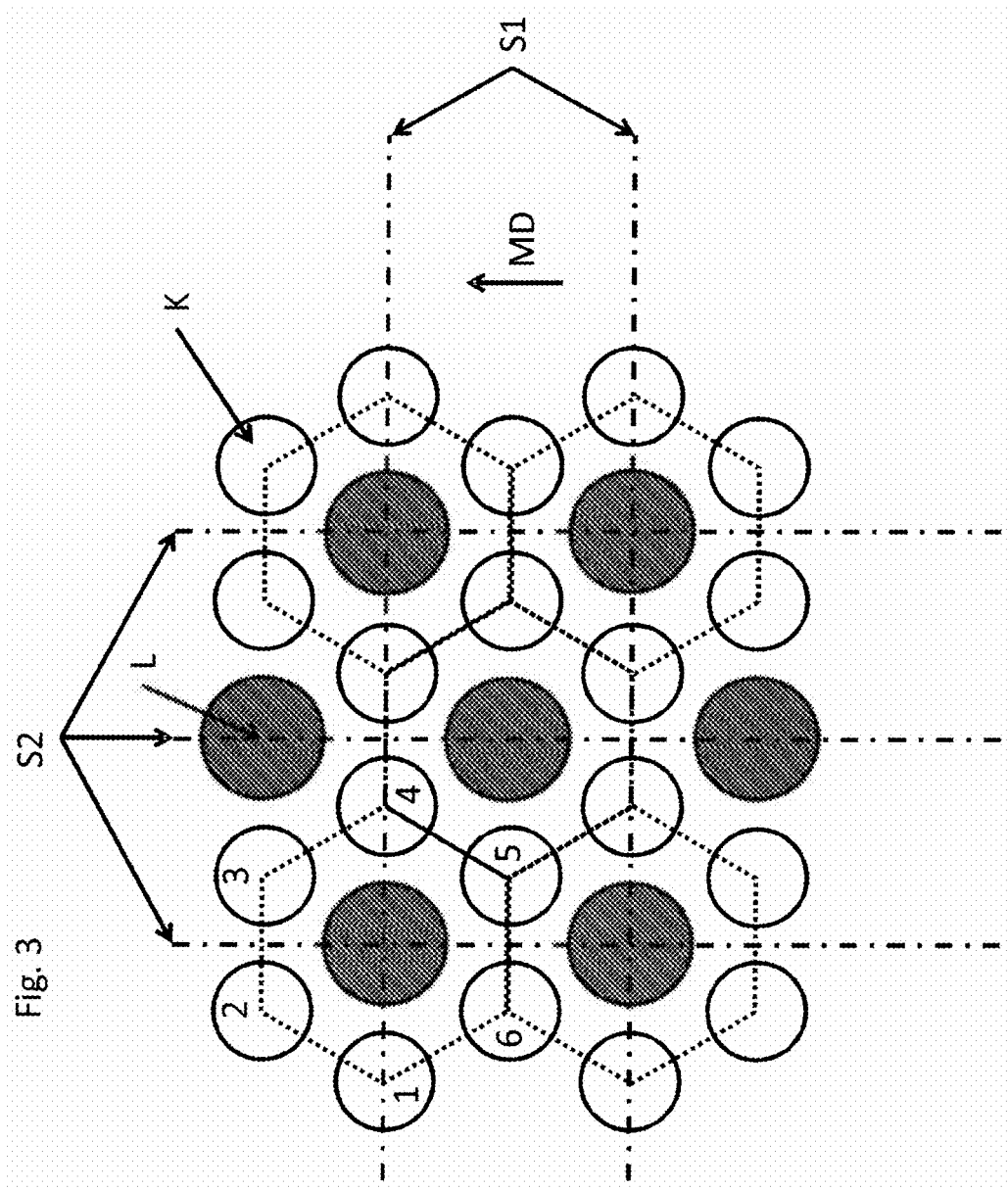

NONWOVEN LAMINATE

CROSS-REFERENCE TO RELATED APPLICATIONS

This application claims the benefit of priority of German Patent Application DE 10 2016 015 445.4, filed on Dec. 23, 2016, the disclosure of which is incorporated herein by reference in its entirety.

BACKGROUND OF THE INVENTION

Disposable articles for sanitary applications, such as e.g. sanitary napkins, diapers and incontinence products, have the purpose of removing body excretions from the skin as quickly as possible in order to avoid skin irritation and to give the user a safe and comfortable feeling. For this purpose, sanitary products are generally structured as follows:
   First layer: top sheet (perforated film or nonwoven fabric)
   Second layer: acquisition and distribution layer, "ADL" (mostly made of nonwoven fabric)
   Third layer: absorbent core (composed of pulp and/or polyacrylic acid fixated in one or more fixation layers (SMS)
   top layer: film to prevent leakage of liquid on the back side The aim of sanitary products contacting the body is to absorb body liquids as quickly as possible and without residue and to bind them to absorbent material that immobilizes the liquid. It is there to be prevented, in particular, that body contact with the liquids persists over a long time and that the liquids escape from the sanitary product in an uncontrolled manner prior to immobilization and soil the underwear or even appear as visible stains on the outer clothing.

In order to achieve this aim, multilayer composites composed of a liner (top sheet), a liquid acquisition and distribution layer, an absorbent core and a film impermeable to liquid have typically been used as clothing protection. These nonwovens and films, which are generally produced as individual layers, are thermally, chemically or ultrasonically bonded to form the functional unit.

However, it has shown that these conventional composites can absorb well and bind only low-viscosity, homogeneous aqueous liquids with a Newtonian flow behavior, such as urine. The reason for this is the predominantly capillary transport mechanism which is based on the fine pore structure of the nonwovens used.

Capillarity, however, has a counterproductive effect on permeability. The finer the pores of a material, the higher the capillary force that can absorb a wetting fluid, but also the higher the frictional force that inhibits liquid transport. As the viscosity of the liquid increases, this inhibition increases yet further. In contrast, coarse pore structures exhibit higher permeability and also allow more viscous fluids a faster passage.

In the case of liquids containing particles, a further inhibiting effect arises, mechanical blocking. Even coarse mesh structures tend to block if the mesh size is not significantly larger than the particle dimension. With nonwovens, such coarse pores within the fiber structure can not be obtained, if at the same time a high demand is posed regarding softness and gentleness to the skin which prohibits extremely coarse and therefore rigid fibers.

Viscous body fluids containing particles include, for example, menstruation liquid, thin intestinal excretions, new born stools, blood, and wound secretions. These liquids are not absorbed and transported by normal nonwoven structures. Only capillary drainage occurs, which is based on the fact that water is removed from the heterogeneous liquids due to the capillary effect, whereby they themselves are thickened. What remains is an even more viscous fluid with a mushy consistency which often leads to irritation and inflammatory irritation following prolonged skin contact.

There has therefore been no lack of attempts to remedy these deficiencies by impressing an overtexture with elevations and depressions or foldings.

For example, patent WO2014068492 describes a method in which a nonwoven with a texture of hollow projections is formed. This nonwoven is able to absorb a certain amount of heterogeneous, viscous fluid, at least in the depressions. However, the fluid remains on the body side and is not passed on within the nonwoven composite.

On the other hand, patent DE10296874 describes a composite material comprising: a first layer containing a plurality of apertures; and a substructure bearing against the first layer, where the substructure and the first layer define a plurality of cavities for accommodating a passage of fluids through the composite material. The disadvantage is that the composite is composed of two individually produced layers which are bonded to each other only after the shaping process. It is therefore not possible to make the perforations of the top layer coincide with the cavities of the lower layer in an ideal manner. Without coinciding, however, the cross-section of the aperture is reduced, which greatly increases the tendency for a blockage.

Known from DE1013627 are ADL layers as textured nonwovens which have a texture of differently compressed fiber regions extending in parallel. Although these nonwovens ensure good liquid distribution in the highly compressed regions, nonwovens produced in this way tend to be rigid and inflexible due to the thermal fixation of the highly compressed regions. Furthermore, absorption of viscous or pasty body excretions containing particles is possible only in the region of the gaps arising between much and less compressed regions. Such nonwovens therefore always require a cover layer in order to cover the possible body excretions above-described.

The use of perforated nonwovens again solves the problem of handling pasty body excretions, but such nonwovens are mechanically not highly loadable due to the perforation. Furthermore, such nonwovens require a downstream ADL layer to evenly distribute the body excretions through the absorbent core. For example, DE 102006033071 is there generic. Two layers are therefore again needed, where only their combination enables purposeful handling of body excretions.

Furthermore, laminates in which filament nonwovens are hydrodynamically bonded to and textured with staple fiber nonwovens are known from the prior art of EP423619. Although the mechanical properties are improved with such combinations, the inadequate handling of pasty body excretions, however, is likewise disadvantageous.

SUMMARY OF THE DISCLOSURE

The object of the invention is therefore to provide a nonwoven laminate which, in addition to sufficient mechanical strength and softness, is also able to absorb pasty body excretions and distribute them in a selective manner within a sanitary product.

The present invention satisfies the object by providing a nonwoven laminate V (see FIG. 1) made of at least two layers composed of a carded nonwoven with a filament nonwoven.

One aspect of the invention is directed to a nonwoven laminate comprising a carded staple fiber nonwoven and a filament nonwoven, which are mechanically bonded by hydraulic needling, and comprise a first and second surface, wherein both the first and second surface of the nonwoven laminate have perforations distributed in a pattern-like manner, where the second surface of the nonwoven laminate has a texture of elevations extending parallel to each other, and the perforations are disposed between these elevations. In one embodiment of the nonwoven laminate the perforations are arranged in a hexagonal pattern, and the elevations extend at an angle of 90° relative to the axis of symmetry S1 which determines the orientation of the pattern of the perforations. In another embodiment of the nonwoven laminate the first surface is formed by the carded nonwoven, and the second surface is formed by the filament nonwoven. In one embodiment the perforations have a circular and/or ellipsoidal and/or irregular shape, and have an aperture area of 0.5 mm$^2$ to 20 mm$^2$, preferably 3 mm$^2$ to 10 mm$^2$. In one embodiment the elevations are oriented in the manufacturing direction, and extend with a spacing of 2 mm to 15 mm, preferably 4 mm to 7 mm. In another embodiment of the nonwoven laminate, the second surface is hydrophilic, and the first surface is less hydrophilic to hydrophobic with respect to the second surface, so that at least one gradient exists between the two surfaces. In one embodiment of the nonwoven laminate, the filament nonwoven is a spunbonded nonwoven or a combination of spunbonded nonwovens with extrusion nonwovens. In one embodiment the carded staple fiber nonwoven layer has a basis weight, according to DIN EN 29073-1, of 5 g/m$^2$ to 80 g/m$^2$, and the filament nonwoven has a basis weight of 5 g/m$^2$ to 40 g/m$^2$. Alternatively the carded staple fiber nonwoven layer basis weight can be 10 g/m$^2$ to 60 g/m$^2$, or 20 g/m$^2$ to 40 g/m$^2$. In one embodiment the filament nonwoven basis weight is 8 g/m$^2$ to 25 g/m$^2$. Alternatively the filament nonwoven basis weight can be 10 g/m$^2$ to 20 g/m$^2$. The staple fibers can comprise thermoplastic polymers, or polyesters, or synthetic cellulosic fibers, or natural cellulosic fibers, or any combinations thereof. Suitable thermoplastic polymers are polyolefins, which can be selected from the group consisting of polypropylene (PP), polyethylene (PE), PP/PE, PP copolymers, and polyacrylates (PA). Suitable polyesters can be selected from the group consisting of polyethyleneterephthalate (PET), PET copolymers, polylactic acid (PLA), and polyethylene furanoates (PEF). Suitable synthetic and natural cellulosic fibers can be selected from the group consisting of cotton, viscose and lyocell. In one embodiment the filament nonwoven comprises one or more thermoplastic polymers selected from the group consisting of PP, PP copolymers, PP/PE and PET/PE.

BRIEF DESCRIPTION OF THE DRAWINGS

FIG. 3 shows the surface pattern of a texturing drum designed according to the invention, for producing the pattern on the textured surface of the nonwoven laminate. See Table 2 for description of Figure labels.

DETAILED DESCRIPTION OF PREFERRED EMBODIMENTS

Figure 1:
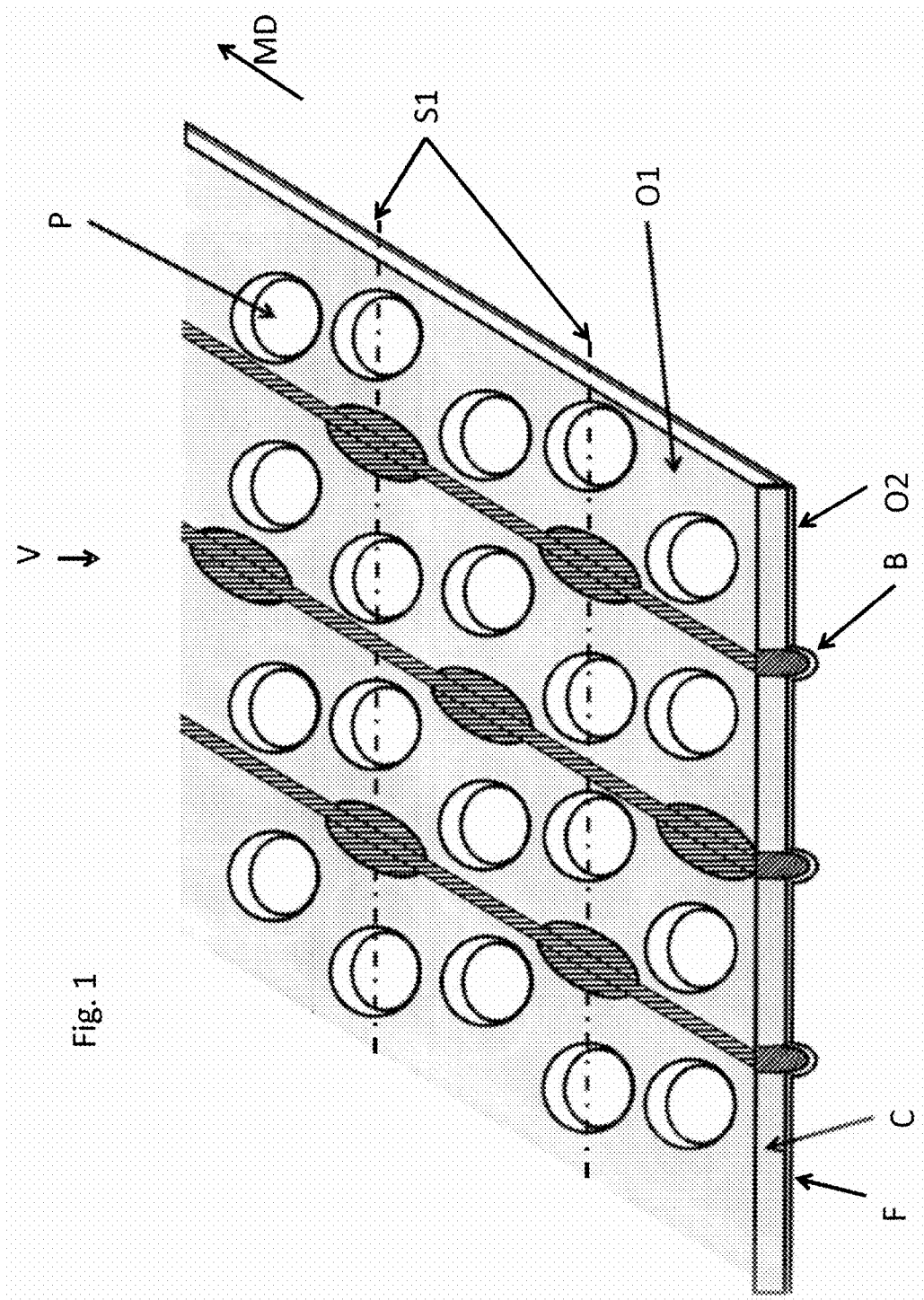
FIG. 1 shows a schematic diagram of one embodiment of the nonwoven laminate. See Table 2 for description of Figure labels.
Figure 2:
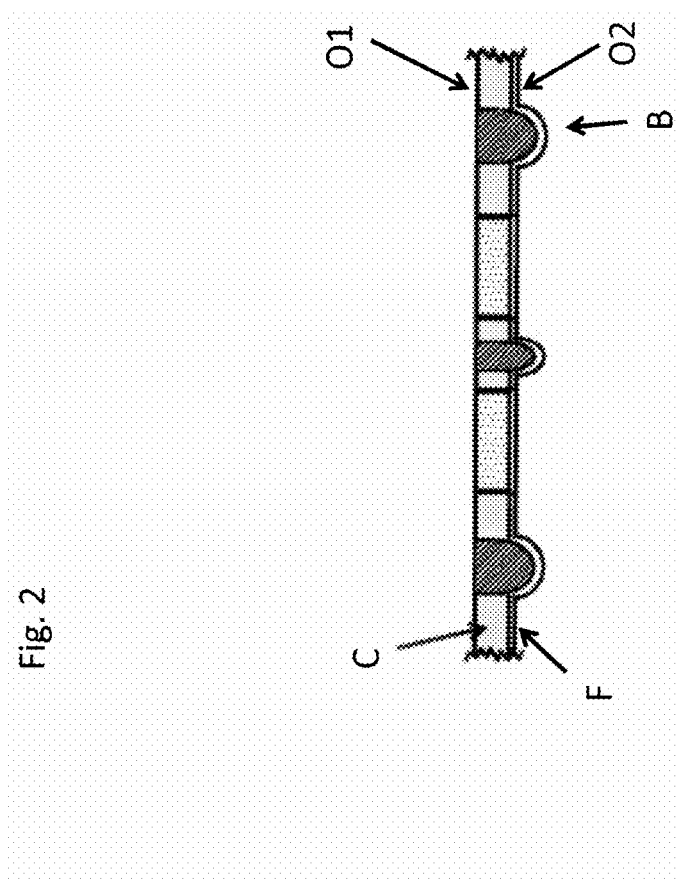
FIG. 2 shows the schematic diagram of a cross section of the nonwoven laminate of FIG. 1. See Table 2 for description of Figure labels.

According to FIG. 1, nonwoven laminate V has two different surfaces:
  Surface 01, which is largely planar and comprises regularly arranged perforations P that penetrate the nonwoven laminate and reach up to surface 02.
  Surface 02 which, in addition to perforations P, comprises elevations B rising from the surface and extending parallel to one another.

This creates channels on surface 02 that extend along surface 02 and are defined laterally by elevations B.

If, for example, a nonwoven laminate V according to the invention is used in a sanitary product, then surface 01 can be arranged facing the user. Surface 02 then faces the absorbent core.

Impinging liquids penetrate through perforations P into the texture. Depending on the viscosity, they are then distributed along the channels on surface 02 by way of two mechanisms:
  a) Low viscosity liquids are transported due to capillary forces within elevations B,
  b) Pasty liquids are transported pressure-driven within the channels.

Pressure-driven means that pressure is applied during use perpendicular to the possible direction of motion of the liquid e.g. in a diaper by sitting, so that the liquid can escape from this pressure along the channels.

Hereinafter, the terms staple fibers, carded nonwoven, filament nonwoven and spin finish are mentioned, and they are defined as follows:

Staple fiber: denotes a fiber of a finite length. Typical fiber lengths are in the range of 10-70 mm, preferably 35-50 mm. The fiber fineness is in the range of 1.0 to 3.3 dtex, preferably 1.3 to 2.2 dtex. The cross-sectional shape of the staple fibers can be either round/ellipsoidal, but other cross sections, such as lobated, are also possible.

The staple fibers used can be synthetic fibers, but also natural fibers.

Without being restricted thereto, staple fibers within the meaning of the present invention are preferably made of thermoplastic polymers such as polyolefins (PP, PE, PP/PE, CoPP, PA . . . ), polyesters (PET, CoPET, PLA, PEF=polyethylene furanoates) and of synthetic and/or natural cellulosic fibers such as cotton, viscose or lyocell. The staple fibers can be a mono-material or used in any mixing ratio relative to each other.

The term carded nonwoven refers to nonwovens produced using staple fibers that are produced in a carding process. The underlying method can be gathered from the book "Vliesstoffe (Nonwovens)", page 136 et. seqq. published by Wiley VCH-Verlag, Weinheim in the year 2012.

The term filament nonwoven denotes nonwovens which were produced in an extrusion process, such as the spunbond process, the meltblown process or the combination of these two processes, the so-called spunbond/meltblown/spunbond, in short S/M/S process, and are thermally hardened by calendaring. Filament nonwovens according to the invention are made of thermoplastic polymers, preferably of polyolefins (PP, PE, PP/PE, CoPP, PA) or polyesters (PET, CoPET, PLA, PEF=polyethylene furanoates). The filament fineness for spunbonded nonwovens is in the range of 1.0 to 3.3 dtex, preferably 1.3 to 2.2 dtex. The underlying production methods can be gathered from the book "Vliesstoffe", page 175 et. seqq. published by Wiley VCH-Verlag, Weinheim in the year 2012.

Spin finish denotes a functional coating of fiber or filament surfaces. The aim is to influence either the processing properties or the properties of use. Examples of these are antistatic agents or hydrophilizing or hydrophobing agents. A basic description can be gathered from the book "Vliesstoffe", page 83 et. seqq. published by Wiley VCH-Verlag, Weinheim in the year 2012.

The term pasty denotes liquids whose viscosity is in the range of 4 to 150 mPas (measured with a rotational viscometer at 20° C.).

The parameters determined there were determined according to the following test methods:
Basis weight according to WSP 130.1, given in g/m²
Rising height according to WSP 010.1, paragraph 7.3, given in mm
Thickness according to WSP 120.6, measuring pressure 0.5 kPa, given in mm
Strike-through according to WSP 70.7, given in s
Rewet according to WSP 70.8, given in g
Run-off following WSP 80.9, 75 ml instead of 50 ml NaCl solution is used in deviation to this standard, the inclined plane has a gradient of 25° instead of 45°. The run-off is calculated according to the following formula:

$$\text{run-off}[\%] = \frac{\text{amount of run-off in } g.}{\text{amount of liquid applied in } g.} * 100$$

To produce nonwoven laminate V according to the invention, a carded nonwoven C made of staple fibers is deposited on a pre-hardened filament nonwoven F, for example a spunbonded nonwoven, and bonded together by way of water jet needling.

The resulting, still untextured pre-composite is then fed to a texturing drum, so as to produce the texture according to the invention by further water jet treatment of the pre-composite.

This texturing drum now has apertures L distributed in a pattern-like manner on the drum surface and perforation elements K projecting from the surface.

By defining the distances of apertures L relative to each other and the arrangement of perforation elements P around apertures L, an accumulation of fibers and filaments displaced by the action of the water jet is caused during the texturing process in such a way that elevations B are formed.

Preferred and without being restricted thereto, the arrangement of perforation elements K is effected in a hexagonal pattern, where perforation elements K each respectively occupy the corner points of the hexagons. An aperture L is arranged at the center of every hexagon defined by the perforation elements.

The orientation of the hexagons on the surface of the texture drum is determined by the axis S1 of symmetry. Axis S1 of symmetry describes the line of symmetry which runs through two opposite corners of the hexagon.

FIG. 3 clarifies this. It schematically shows the spatial arrangement of perforation elements K, for example, in the form of cones, on the surface of the texture drum. For better recognition of the hexagonal structure, the cone tips were connected with dotted reference lines.

Also for identification, the cone tips of a hexagon were provided with numbers. Line S1 of symmetry results from the connection of cone tips 1 and 4. The position of apertures L along line S2 of symmetry can also be seen in FIG. 3. It connects the centers of apertures L and is offset by 90° relative to the line S1 of symmetry.

Line S1 of symmetry can be offset by 90°, as shown in FIG. 3, i.e. run transverse to the manufacturing direction MD, but it can also be selected at an arbitrary angle between 0 and 90° relative to the manufacturing direction MD. The final orientation depends on the subsequent intended use and the desired distribution direction for liquids in a sanitary product.

When manufacturing nonwoven laminate V according to the invention, it is to be noted that the side of the pre-composite on which the filament nonwoven is arranged comes to rest on the texture drum. That side of the pre-composite forms side 02 in the later nonwoven laminate. The side on which the carded nonwoven is located is side 01 in the later nonwoven laminate.

During the texturing process, the pre-composite is pressed onto perforation elements K by the impinging jets of water. As a result of the water pressure prevailing there, perforation elements K penetrate into the pre-composite, so that the pre-composite, in particular the filament nonwoven fabric, tears at these points and perforations P are thus formed in the nonwoven composite V according to the invention. The fibers/filaments of the pre-composite are there displaced laterally along the flanks of perforation elements K.

It has surprisingly been found that the displaced fibers accumulate along axis S2 of symmetry and are swirled together by the water jet treatment due to the arrangement selected according to the invention of perforation elements K in combination with apertures L. These swirls consisting of displaced fibers form elevations B claimed according to the invention, which run continuously along axis S2 of symmetry.

This is explained by the interaction of the orientation according to the invention of perforation elements K on the texture drum in combination with apertures L.

During the perforation process, the fibers and filaments displaced by perforation elements K accumulate primarily along axis S2 of symmetry and are forced into apertures L by the prevailing water pressure. The filaments and fibers present in carded nonwoven fabric C and filament nonwoven F there bridge the distance between two apertures L along axis S2 of symmetry, so that the swirls and consequently elevations B according to the invention arise continuously along axis S2 of symmetry. A portion of the fiber of carded nonwoven fabric C is there forced through the filament nonwoven.

As can be seen schematically in FIG. 1, the width of elevations B varies there. At the center of a hexagon, elevations B are wider than in the region between perforations P.

After the texturing treatment has thus been performed, nonwoven laminate V according to the invention is obtained which has a flat, perforated surface 01 and a perforated surface 02 provided with elevations B.

The staple fiber layer on side 01 forms a predominantly smooth side with pleasant softness and high wearing comfort, whereas side 02 around the perforations is forced into the cavities of the texture drum as a result of fiber compaction, thereby forming the line-shaped elevations B. An essential aspect there is the compaction of the fibers around apertures P. Due to this compaction, elevations B are stabilized and sustained even under pressure. Elevations B, on the one hand, form intermediate cavities in the form of channels which are highly permeable to, in particular, viscose liquids and those containing particles, on the other hand, the compacted fibers form parallel strands with high capillarity within elevations B which are also able to actively absorb low-viscosity liquids.

A preferred embodiment of the invention provides that axis S1 of symmetry extends transversely to the manufacturing direction MD. In the later use in a sanitary product, side 01 formed by the staple fiber layer is oriented toward the skin side as a top layer, whereas the filament layer on side 02 is oriented toward the absorbent core with the channel structures enclosed by it. Since perforations P open end-to-end and directly into the channel structures, the liquid absorption is significantly improved over prior art.

The orientation of the channels and elevations B in the machine direction allows for directional liquid transport which provides optimal liquid distribution within the sanitary product. At the same time, the capillarity of the fiber strands within elevations B and the high permeability of the macroscopic channels come into effect.

The body fluids are directed along the channels directly to the absorbent core. Although the latter is not able to absorb the fluids in their entirety, the polymeric absorbers, however, due to their gel-like structure, are able to drain the body fluids much more capillarily than fiber nonwoven fabrics would be able to do. This leads to extensive dewatering, volume reduction and immobilization of fluid residues in the cavity structures of the composite material.

Since capillarity is associated with fine pores, polymeric superabsorbers with their pores of molecular dimension are capable of developing greater capillary forces by orders of magnitude than fine-pored fibrous nonwovens. The dewatering of the heterogeneous fluids, which are themselves of a gel-like nature in a thickened state, therefore succeeds to a greater extent than if the fluids came in contact with fibers only on the cover layer and have too large a distance from the absorbent core.

In an exemplary embodiment of the nonwoven laminate of the present invention, a pile of polyethylene terephthalate staple fibers with a titer of 1.3 dtex and a staple length of 38 mm and a face weight of 35 g/m² was deposited onto a filament nonwoven of the type spunbonded fabric made of polypropylene filaments having a basis weight of 10 g/m².

The layers of the resulting structure are bonded to each other by way of water jet needling at an average pressure of 90 bar, so that the pre-composite is formed.

Subsequently, the pre-composite is fed to a texturing unit, consisting of a texture drum and two bars provided with perforated strips for creating the jets of water. A pressure of 180 bar at the water jet bars is generated by high pressure pumps.

The texture drum has a surface designed according to the invention, in which, based on FIG. 3,
- the perforation elements are composed of cones whose cone base on the texture drum has a diameter of 1.8 mm,
- The perforation elements are arranged in the shape of a regular hexagon with an edge length of 3.8 mm,
- apertures L are arranged centrally within the hexagon,
- apertures L are configured as circles with a diameter of 4.4 mm.

After texturing, a hydrophilic spin finish was applied to surface 02 on one side, so that nonwoven composite V has two differently hydrophilic sides. Surface 01 is less hydrophilic than side 02, so that liquids impinging on side 01 are quickly passed through the perforations to side 02.

The textured nonwoven laminate has the following properties after completion of the treatment:

TABLE 1

| Aperture diameter (linear) | [mm] | 1.7 |
| Spacing of elevations B (linear, measured along the line of symmetry S2) | [mm] | 4.8 |
| Basis weight | [g/m²] | 45 |
| Thickness | [mm] | 1 |
| Strike-through | [s] | 2.0 |
| Rewet | [g] | 0.08 |
| Rising height (after 120 s) | [mm] | 30 |
| Run-off (inclination angle 25°) | [%] | 0 |

In addition to the data given in the exemplary embodiment, the textures of a nonwoven laminate V embodied according to the invention can also be influenced by the shape of perforation elements P. Perforation elements P need only be able to tear open the pre-composite at the defined locations for creating an application-dependent aperture area of 0.5 mm² to 20 mm², preferably of 3 mm² to 10 mm².

Small aperture areas up to 1 mm² are mainly suitable for management of low viscous liquids, aperture areas from 3 mm² are suitable for higher viscous fluids. The aperture area is limited toward the top by the stability of the nonwoven laminate. Aperture areas larger than 20 mm² lead to a nonwoven laminate having only insufficient mechanical strength.

The spacing between elevations B can be selected in a range of 2 mm to 15 mm, more preferably 4 mm to 7 mm. The selection here as well depends on the purpose of use. Small spacing causes a higher restoring force in the composite, larger spacing causes a softer nonwoven.

The degree of formation of elevations B is further influenced by the basis weight of the carded nonwovens and/or the filament nonwovens used. The higher the basis weight, the more fiber mass can be displaced during texturing, accordingly the more pronounced is the degree of formation of elevations B. Basis weight ranges according to the invention for carded nonwoven C are at 5 g/m² to 80 g/m² and preferably from 20 g/m² to 40 g/m². For filament nonwoven, a basis weight from 5 g/m² to 40 g/m², preferably from 10 g/m² to 20 g/m² is usable.

Also the type and the proportion of spin finish on nonwoven laminate V is to be regarded depending on the application. As a result of the water jet process, the spin finish present on the fibers as a processing aid is largely washed off, so that nonwoven composite V is initially hydrophobic.

In order to now obtain the desired hydrophilicity, the nonwoven laminate must be subsequently treated with a hydrophilic spin finish. Layers of 0.05 to 1.0 mass percent are typical, where a range of 0.2 to 0.8 mass percent is preferred.

The layering of spin finish can take place on one side, preferably on surface 02 of the nonwoven laminate according to the invention. But two-sided layering is also possible.

Preference is given to spin finishes that cause more hydrophilic properties on surface 02 than on surface 01, so that a gradient is established between the two surfaces.

In addition to the use in personal sanitary products, nonwoven laminates embodied according to the invention can also be used in other fields, such as cleaning wipes, disinfectant wipes.

TABLE 2

List of Drawing and Figure Labels

| | |
|---|---|
| V = | nonwoven laminate |
| P = | perforation in the nonwoven laminate |
| 01 = | untextured surface of the nonwoven laminate |
| 02 = | textured surface of the nonwoven laminate |
| B = | elevation in the nonwoven laminate |
| C = | carded nonwoven |
| F = | filament nonwoven |
| S1 = | axis 1 of symmetry |
| S2 = | axis 2 of symmetry |
| K = | perforation elements on the texture shell |
| L = | apertures in the texture shell |
| MD = | manufacturing direction |
| 1-6 = | cone tips |

What is claimed is:

1. A nonwoven laminate comprising a carded staple fiber nonwoven and a filament nonwoven, which are mechanically bonded by hydraulic needling, and comprising a first and second surface, wherein
both the first and second surface of said nonwoven laminate have perforations distributed in a pattern,
the second surface of said nonwoven laminate has a texture of elevations extending parallel to each other, and
said perforations are disposed between said elevations,
wherein said perforations are arranged in a hexagonal pattern,
wherein each of said elevations is continuous and line-shaped and comprises compacted fibers of the carded staple fiber nonwoven and the filament nonwoven, wherein the compacted fibers form parallel strands within the elevations for capillary liquid transport and any two of the elevations adjacent to each other define there-between a channel for pressure-driven liquid transport and said line-shaped elevations extend at an angle of 90° relative to an axis of symmetry S1 which determines the orientation of the hexagonal pattern of said perforations.

2. The nonwoven laminate according to claim 1, wherein said first surface is formed by said carded nonwoven, and said second surface is formed by said filament nonwoven.

3. The nonwoven laminate according to claim 1, wherein said perforations have a circular and/or ellipsoidal and/or irregular shape, and wherein an aperture area of each perforation is in a range of 0.5 mm$^2$ to 20 mm$^2$.

4. The nonwoven laminate according to claim 3, wherein the aperture area of each perforation is in a range of is 3 mm$^2$ to 10 mm$^2$.

5. The nonwoven laminate according to claim 1, wherein said elevations are oriented in the manufacturing direction, and a spacing between said elevations is in a range of 2 mm to 15 mm.

6. The nonwoven laminate according to claim 5, wherein the spacing between said elevations is in a range of 4 mm to 7 mm.

7. The nonwoven laminate according to claim 1, wherein said second surface is hydrophilic, and said first surface is less hydrophilic to hydrophobic with respect to said second surface, so that at least one gradient exists between the two surfaces.

8. The nonwoven laminate according to claim 1, wherein said filament nonwoven is a spunbonded nonwoven or a combination of spunbonded nonwovens with extrusion nonwovens.

9. The nonwoven laminate according to claim 1, wherein said carded staple fiber nonwoven has a basis weight according to DIN EN 29073-1 of 5 g/m$^2$ to 80 g/m$^2$, and said filament nonwoven has a basis weight of 5 g/m$^2$ to 40 g/m$^2$.

10. The nonwoven laminate according to claim 9, wherein said carded staple fiber nonwoven basis weight is 10 g/m$^2$ to 60 g/m$^2$.

11. The nonwoven laminate according to claim 9, wherein said carded staple fiber nonwoven basis weight is 20 g/m$^2$ to 40 g/m$^2$.

12. The nonwoven laminate according to claim 9, wherein said filament nonwoven basis weight is 8 g/m$^2$ to 25 g/m$^2$.

13. The nonwoven laminate according to claim 9, wherein said filament nonwoven basis weight is 10 g/m$^2$ to 20 g/m$^2$.

14. The nonwoven laminate according to claim 13, wherein said staple fibers comprise thermoplastic polymers, or polyesters, or synthetic celluloses, or natural celluloses, or any combinations thereof.

15. The nonwoven laminate according to claim 14, wherein said staple fibers comprise said thermoplastic polymers, wherein said thermoplastic polymers are polyolefins.

16. The nonwoven laminate according to claim 15, wherein said polyolefins are selected from the group consisting of polypropylene (PP), polyethylene (PE), PP/PE, PP copolymers, and polyacrylates (PA).

17. The nonwoven laminate according to claim 14, wherein said polyesters are selected from the group consisting of polyethyleneterephthalate (PET), PET copolymers, polylactic acid (PLA), and polyethylene furanoates (PEF).

18. The nonwoven laminate according to claim 14, wherein said synthetic celluloses are selected from the group consisting of viscose and lyocell and said natural celluloses are cotton.

19. The nonwoven laminate according to claim 13, wherein said filament nonwoven comprises one or more thermoplastic polymers selected from the group consisting of PP, PP copolymers, PP/PE and PET/PE.

* * * * *